(12) United States Patent
Lin et al.

(10) Patent No.: US 10,925,981 B2
(45) Date of Patent: Feb. 23, 2021

(54) HEXA-LACTOSIDE-TRIAZANONANE TRIACETIC ACID (NOTA) DERIVATIVE, METHOD FOR RADIOLABELING HEXA-LACTOSIDE POSITRON EMISSION TOMOGRAPHY (PET) IMAGING AGENT FOR LIVER RECEPTOR WITH GA-68, AND HEXA-LACTOSIDE PET IMAGING AGENT FOR LIVER RECEPTOR

(71) Applicant: Institute of Nuclear Energy Research, Atomic Energy Council, Executive Yuan, R.O.C, Taoyuan (TW)

(72) Inventors: Wuu-Jyh Lin, Taoyuan (TW); Mei-Hui Wang, Taoyuan (TW); Hung-Man Yu, Taoyuan (TW); Kun-Liang Lin, Taoyuan (TW); Yan-Feng Jiang, Taoyuan (TW); Rui-Yu Chen, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 154 days.

(21) Appl. No.: 16/200,833

(22) Filed: Nov. 27, 2018

(65) Prior Publication Data
US 2019/0343971 A1   Nov. 14, 2019

(30) Foreign Application Priority Data

May 9, 2018   (TW) .................................. 107115646

(51) Int. Cl.
| | |
|---|---|
| A61K 51/00 | (2006.01) |
| A61M 36/14 | (2006.01) |
| A61K 51/04 | (2006.01) |
| C07B 59/00 | (2006.01) |
| C07H 15/06 | (2006.01) |

(52) U.S. Cl.
CPC ........ *A61K 51/0497* (2013.01); *C07B 59/005* (2013.01); *C07H 15/06* (2013.01); *A61K 51/0482* (2013.01); *C07B 2200/05* (2013.01)

(58) Field of Classification Search
None
See application file for complete search history.

(56) References Cited

U.S. PATENT DOCUMENTS 9,040,017 B2 *   5/2015  Wang ...................... A61P 43/00
424/1.11

OTHER PUBLICATIONS

Lang et al. (Bioconj. Chem. 2011, 22, 2415-2422).*
Ebenhan et al. (Mol. Imaging Biol. 2017, 19, 469-482).*
Sang Kil Ha-Kawa et al., A Quantitative Model of Technetium-99m-DTPA-Galactosyl-HSA for the Assessment of Hepatic Blood Flow and Hepatic Binding Receptor, Journal of nuclear energy reserach, 2018, 2233-2240.
Wenjiang Yang et al., Synthesis and biological evaluation of 99mTc-DMP-NGA as a novel hepatic asialoglycoprotein receptor imaging agent, Applied Radiation and Isotopes, 2010, 68, 105-109.
Jaeyeon Choi et al., Ga-68-labeled neolactosylated human serum albumin (LSA) for PET imaging of hepatic asialoglycoprotein receptor, Nuclear Medicine and Biology, 2015, 42, 53-58.
Reiko T. Lee et al., New and more efficient multivalent glycoligands for asialoglycoprotein receptor of mammalian hepatocytes, Bioorganic & medicinal chemistry, 2011, 19, 2494-2500.
Roland Haubner et al., Development of 68Ga-labelled DTPA galactosyl human serum albumin for liver function imaging, European Journal of Nuclear Medicine and Molecular Imaging, 2013, 40, 1245-1255.
Roland Haubner et al., [68Ga]NOTA-Galactosyl Human Serum Albumin: a Tracer for Liver Function Imaging with Improved Stability, Molecular Imaging & Biology, 2017, 19, 723-730.
Mei-Hui Wang et al., The specificity and accuracy of 111In-hexavalent lactoside in estimating liver reserve and its threshold value for mortality in mice, Journal of Hepatology, 2015, 63, 370-377.

* cited by examiner

*Primary Examiner* — Michael G. Hartley
*Assistant Examiner* — Melissa J Perreira
(74) *Attorney, Agent, or Firm* — Locke Lord LLP; Tim Tingkang Xia, Esq.

(57) ABSTRACT

The present invention provides a hexa-lactoside-triazanonane triacetic acid (NOTA) derivative, a method for radiolabeling a hexa-lactoside positron emission tomography (PET) imaging agent for a liver receptor with Ga-68, and a hexa-lactoside PET imaging agent for a liver receptor. The hexa-lactoside-NOTA derivative is a conjugate of six chains of lactose with NOTA obtained by conjugating hexa-lactoside to a chelating agent p-thiocyanate-benzyl-triazanonane diacetic acid-glutamic acid in the presence of triethyl amine/dimethyl formamide as a solvent. The radiolabeling method comprises labeling with Ga-68 at room temperature. According to the present invention, the labeling effect is stable, the labeling efficiency of the labeled product is greater than 95%, the labeled product is highly stable and the radiochemical purity is still greater than 90% after 4 hours.

3 Claims, 11 Drawing Sheets

HEXA-LACTOSIDE-TRIAZANONANE TRIACETIC ACID (NOTA) DERIVATIVE, METHOD FOR RADIOLABELING HEXA-LACTOSIDE POSITRON EMISSION TOMOGRAPHY (PET) IMAGING AGENT FOR LIVER RECEPTOR WITH GA-68, AND HEXA-LACTOSIDE PET IMAGING AGENT FOR LIVER RECEPTOR

CROSS-REFERENCE TO RELATED APPLICATION

This application also claims priority to Taiwan Patent Application No. 107115646 filed in the Taiwan Patent Office on May 9, 2018, the entire content of which is incorporated herein by reference.

TECHNICAL FIELD

The present disclosure relates to the technical field of imaging agent, and more particularly to a method for preparing a polylactoside positron emission tomography (PET) imaging agent, and an imaging agent prepared therewith.

BACKGROUND

One-tenth of the world's population suffers from chronic hepatitis, which constitutes a population having high risk of liver cirrhosis, and liver cancer. When the number of reserved hepatocytes is too low because of excessive tumor growth, undue operation, or acute liver inflammation, individuals may die from liver failure. In general, the physicians empirically make a decision based on traditional computed tomography that if 70% of the liver is excised, an individual can still be alive. However, it is difficult to determine the number of remaining surviving hepatocytes in an individual with diffuse liver cancer or liver cirrhosis solely in accordance with the size of the liver. Therefore, there is a need to establish a method for accurately assessing the number of reserved hepatocytes. A preoperative evaluation is needed to get to know how many hepatocytes survive, and also the number of reserved hepatocytes needs to be evaluated periodically after the hepatectomy of hepatocellular carcinoma and liver transplantation, to really understand the condition of liver recovery and maintenance. Clinically, no liver number threshold has been established to assess whether liver replacement is necessary. Therefore, it is an important milestone in setting a liver number threshold in clinic to develop an inspection technique that can accurately quantify the number of reserved hepatocytes.

Professors Aswell and Morell found in 1968 that a very special receptor known as asialoglycoprotein receptor is present on the surface of normal hepatocytes. The asialoglycoprotein receptor strongly binds to a glycopeptide with a terminal lactosyl or galactosyl group. By taking advantage of the characteristic, many asialoglycoprotein receptor imaging markers are developed to evaluate the quality of remaining liver.

Professor Ha-Kawa proposed Tc-99m diethylenetriamine pentaacetic acid-galactosamine-albumin in 1991, and the Tc-99m diethylenetriamine pentaacetic acid-galactosamine-albumin has ever been put into use in clinic (manufactured by Nihon Medi-Physics). The imaging results showed that there is statistically significant difference in the absorption of Tc-99m diethylenetriamine pentaacetic acid-galactosamine-albumin between normal individuals and individuals with chronic liver cirrhosis (Ha-Kawa S K, Tanaka Y. A quantitative model of technetium-99m-DTPA-galactosyl-HSA for the assessment of hepatic blood flow and hepatic binding receptor. J Nucl Med 1991; 32(12):2233-40).

Professor Yang published data on biodistribution of Tc-99m galactosamine-albumin in 2010. The results showed that the absorption is interfered with the background of up to 30% (Yang W, Mou T, Zhang X, Wang X. Synthesis and biological evaluation of (99m)Tc-DMP-NGA as a novel hepatic asialoglycoprotein receptor imaging agent. Appl Radiat Isot 2010; 68(1):105-9). Due to the possible shortage of Tc-99m sources, Ga-68 DTPA-GSA is developed. Particularly, the Ga-68 solution specification has passed the clinical review in Europe and is listed in the European Pharmacopoeia. Moreover, PET imaging device becomes more and more popular, which will necessarily promote the development of Ga-68 imaging marker.

In 2013, Professor Haubner et al. compared the liver targeting performances of both Ga-68 DTPA-GSA and Tc-99m DTPA-GSA. The biological performances are very similar in terms of the dynamic time versus absorption activity curve or the liver uptake; however, the stability of the labeled products in the serum is inconsistent. Specifically, Tc-99m DTPA-GSA still remains stable after 4 hours, while Ga-68-DTPA GSA is less stable, and remains stable in less than 30 minutes. In addition to GSA, Tc-99m and Ga-68 lactoalbumin imaging agents are also developed. Lactose consists of galactose and glucose, where the terminal galactose structure strongly binds to the asialoglycoprotein receptor. Moreover, lactose is much cheaper than galactose, which facilitates the reduction of costs.

In 2015, Choi et al. developed Ga-68-SCN-Bn-NOTA-lactoalbumin (Ga-68-NOTA-LSA) with 2-(p-isothiocyanatobenzyl)-1,4,7-triazacyclononane-1,4,7-triacetic acid (SCN-Bn-NOTA), and experiments were conducted therewith. According to the test results from Choi, Ga-68-NOTA-LSA can achieve a labeling efficiency of 95% or more within 10 min under a labeling condition of pH 4.8-6. Sign yield, and is very stable in serum at 37° C., over a time at least 4 hours (Choi J, Jeong J M, Yoo B C, Hong M K, Kim Y J, Lee Y S, et al. Ga-68-labeled neolactosylated human serum albumin (LSA) for PET imaging of hepatic asialoglycoprotein receptor. Nucl Med Biol 2015; 42(1):53-8). It can be seen that the choice of chelating agent is critical to the stability of the overall marker if the single photon imaging marker is switched to the PET imaging marker. Although Choi et al.'s biodistribution study showed that Ga-68-NOTA-LSA does not have the background interference of GSA, Ga-68-NOTA-LSA is based on protein, and is still a biological preparation upon application as specified by the pharmaceutical regulations. The cost required for passing the test of drug regulatory authorities is much higher than those small molecule peptides. Instead, a peptide-type imaging marker has its advantages and opportunities.

In 2011, Professor Lee proposed that polylactopeptide may be a novel asialoglycoprotein receptor imaging marker (Lee R T, Wang M H, Lin W J, Lee Y C. New and more efficient multivalent glyco-ligands for asialoglycoprotein receptor of mammalian hepatocytes. Bioorg Med Chem 2011; 19(8):2494-500). In 2015, the Institute of Nuclear Energy Research developed Indium-111-polylactopeptide and carried out studies on its characteristics. It is confirmed in a series of animal models of acute hepatitis, hepatocellular carcinoma, and hepatotomy that the peptide-type indium-111-polylactoside, as an asialoglycoprotein receptor imaging agent, does have a characteristic of low background value, can effectively distinguish the differences between mice with hepatic diseases such as liver cancer and acute hepatitis and normal mice, and results in a contrast value that is linearly related to the number of the reserved hepatocytes. The Institute of Nuclear Energy Research also proposed for the first time that when the reserved hepatocytes in individual mice is less than 25%, the individual will die from liver failure.

Although the peptide-type indium-111 polylactoside imaging agent has been proved to be an approach with excellent specificity and accuracy in preclinical tests, indium-111 is a nuclide produced by a cyclotron, which has limited areas of use, and cannot be obtained easily.

SUMMARY

In view of the above, the present invention provides a hexa-lactoside-NOTA derivative, a method for radiolabeling a hexa-lactoside positron emission tomography (PET) imaging agent for a liver receptor with Ga-68, and a hexa-lactoside PET imaging agent for a liver receptor, to solve the problem of limited use of indium-111 due to the non-popularization.

The present invention mainly aims at providing a hexa-lactoside-NOTA derivative, which is a conjugate of six chains of lactose with NOTA obtained by conjugating hexa-lactoside to a chelating agent p-thiocyanate-benzyl-triazanonane diacetic acid-glutamic acid (e.g. p-SCN-benzyl-NODA-GA) in the presence of a basic solvent such as triethyl amine, and suitable for chelating Ga-68 for use as a PET imaging agent for a liver receptor.

In some embodiments of the present invention, the hexa-lactoside is AHA-Asp[DCM-Lys(ah-Lac)$_3$]$_2$.

In some embodiments of the present invention, the NOTA is p-thiocyanate-benzyl-triazanonane diacetic acid-glutamic acid (e.g. p-SCN-benzyl-NODA-GA).

Another object of the present invention is to provide a method for radiolabeling a hexa-lactoside PET imaging agent for a liver receptor with Ga-68, which comprises reacting 3-valent Ga-68 and a NOTA conjugate of six chains of lactose with sodium acetate buffer (pH 4-5) in a freeze drying ampoule at room temperature.

In some embodiments of the present invention, the reaction at room temperature is continued for 15 min.

In some embodiments of the present invention, the reaction at room temperature takes place at pH 4-5.

In some embodiments of the present invention, the hexa-lactoside-thiocyanate-benzyl-triazanonane diacetic acid-glutamic acid in the labeled product is chelated with Ga-68 by 6 coordination bonds.

Another object of the present invention is to provide a hexa-lactoside PET imaging agent for a liver receptor, which has a structure below:

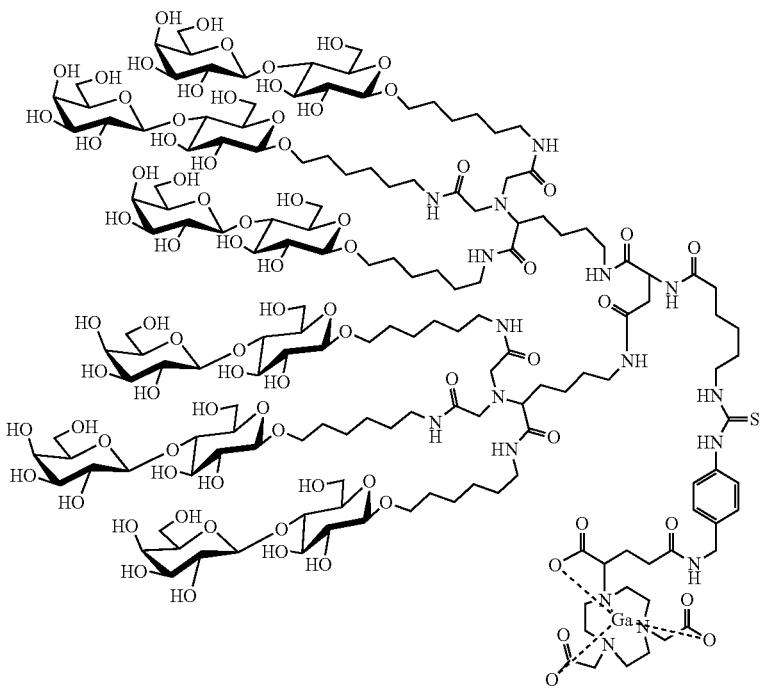

In some embodiments of the present invention, the labeled product is prepared through the radiolabeling method above.

According to the hexa-lactoside-NOTA derivative, the method for radiolabeling a hexa-lactoside PET imaging agent for a liver receptor with Ga-68, and the hexa-lactoside PET imaging agent for a liver receptor disclosed in the present invention, during the use for imaging, only 1.5 mL of normal saline needs to be added and mixed uniformly, and then a sample is taken and used without any purification steps, where the specific activity is more than 4.16 MBq/μg. According to the present invention, the labeling effect is stable, the labeling efficiency of the labeled product is greater than 98%, the labeled product is highly stable and the radiochemical purity is still greater than 98% after 4 hours.

DETAILED DESCRIPTION OF DISCLOSED EMBODIMENTS

Hereinafter, the detailed features and advantages of the present invention will be described in detail in the embodiments. The disclosure is sufficient to enable any person skilled in the art to understand and implement the technical contents of the present invention. Those skilled in the art can easily understand the related objects and advantages of the present invention from the disclosure of the specification, the claims and the drawings of the present invention. The following examples are provided for further illustrating the concept of the present invention in detail, instead of limiting the scope of the present invention in any way.

In an embodiment of the present invention, Ga-68 is used as a nuclide and produced by using a Ga-68 generator. Therefore, with the Ga-68 generator, Ga-68 can be easily produced and used for labeling, which brings convenience in use. In addition, Ga-68 is a positron nuclide. The positron images obtained therewith are clearer than those obtained by single photon imaging. Ga-68 has a half-life of only 68 minutes, which is very suitable for use in targeted angiography and diagnosis. In an embodiment of the present invention, hexa-lactoside is conjugated to a suitable chelating agent that can be labeled with the radioactive isotope Ga-68, to develop a Ge-68-PET imaging agent for a liver receptor.

For the selection of the metal chelating agent, DTPA and 1,4,7,10-tetraazacyclododecane-N,N',N'',N'''-tetraacetic acid (DOTA) are common metal chelating agent. Since Ga-68 is relatively small, a cyclic chelating agent such as 1,4,7-triazanonane triacetic acid (NOTA) can more tightly sequester Ga-68-sized metals, so the following series of NOTA chelating agents are used for conjugation with hexa-lactoside, including, diBocNOTA (di-tert-butyloxycarbonyl protected NOTA), NHS-NOTA (N-hydroxysucciniimide triazanonane), and p-NCS-Bn-NODA-GA (2,2'-(7-(1-carboxy-4-((4-isothiocyanatobenzyl)amino)-4-oxobutyl)-1,4,7-triazonane-1,4-diyl)diacetic acid (e.g. p-SCN-benzyl-NODA-GA), and most suitable chelating agents are selected therefrom.

The features and implementation of the present invention are described in detail below with reference to preferred examples.

Example 1. Preparation of Hexa-Lactoside

Figure 1:
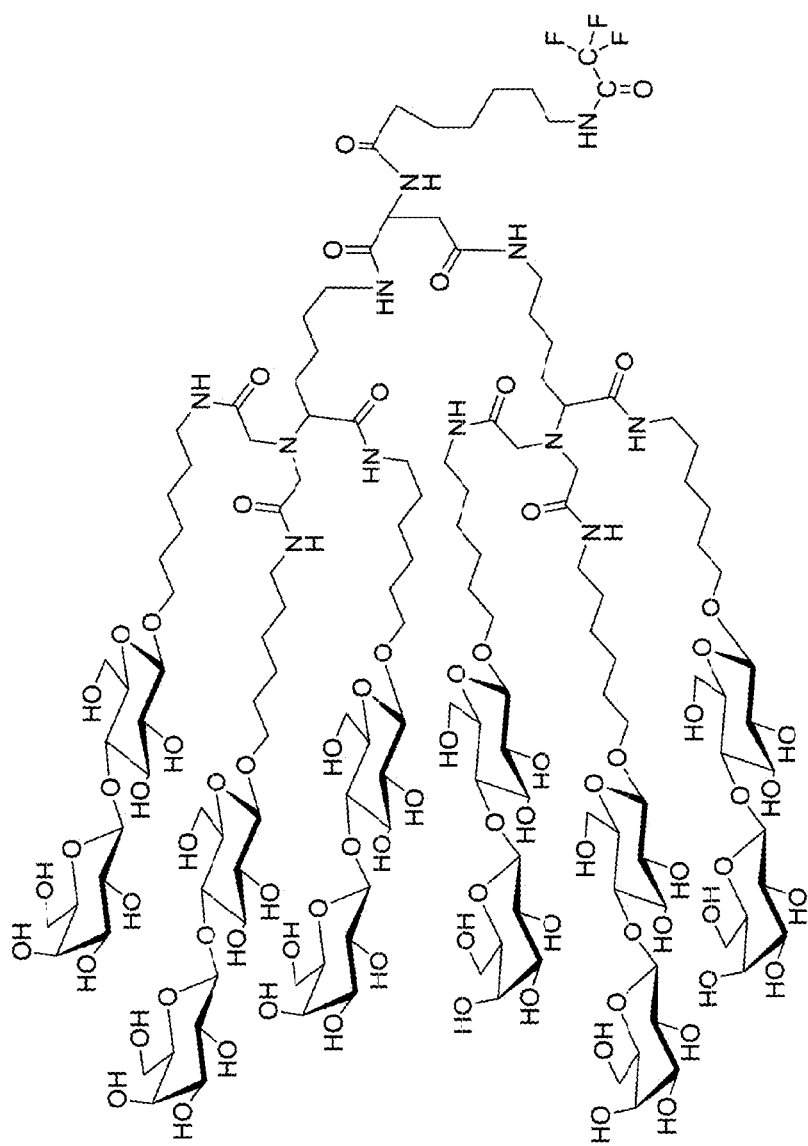
FIG. 1 shows a hexa-lactoside structure protected with a trifluoroacetate.

The structure of the white solid hexa-lactoside protected with a trifluoroacetate is shown in FIG. 1. The analysis data of the compound:

$C_{140}H_{247}F_3N_{12}O_{76}$; TLC RP-18 (MeOH/1% TFA=5:5) $R_f$=0.26; $^1$H NMR (300 MHz, $D_2O$) δ 4.46 (t, J=6.0 Hz), 4.30 (d, J=7.8 Hz), 4.29 (d, J=7.8 Hz), 3.83-3.06 (m), 2.53 (dd, J=14.7, 6.0 Hz), 2.41 (dd, J=14.7, 8.4 Hz), 2.12 (t, J=6.9 Hz), 1.46-1.19 (m); $^{13}$C NMR (75 MHz, $D_2O$) δ 176.50, 174.32, 173.28, 172.25, 171.35, 103.08, 102.22, 78.53, 75.50, 74.90, 74.61, 72.99, 72.66, 71.09, 70.66, 68.69, 66.43, 61.17, 60.26, 56.03, 51.07, 39.72, 39.33, 39.19, 35.46, 28.87, 28.49, 27.65, 26.05, 25.54, 24.92, 23.23; ESI-HRMS: calcd for 1124.5350, found: m/z 1124.5314 $[M+3H]^{+3}$.

The deprotection step was as follows. The compound (626 mg, 0.186 mmol) was dissolved in triethylamine/ethanol/water (ratio by volume=1:1:8, 12 mL) and stirred overnight at room temperature (approximately 15 hrs). After the reaction was completed, the reaction solution was concentrated under reduced pressure and dried. Next, methanol (about 20 mL) was added and ultrasonicated (for 5 min). A white solid was precipitated out, which was pipetted into a centrifuge tube and centrifuged at 3000 rpm for two minutes. The methanolic supernatant was pipetted out and the lower solid was dried at a high vacuum level to obtain the deprotected hexa-lactoside compound (HexaLac, 503 mg) (yield 83%). The analysis data of the compound obtained: $C_{138}H_{248}N_{12}O_{75}$; TLC RP-18 (MeOH/1% TFA=5:5) $R_f$=0.68; ESI-MS: calcd for 1092.53, found: m/z 1092.97 $[M+3H]^{+3}$. The hexa-lactoside is AHA-Asp[DCM-Lys(ah-Lac)$_3$]$_2$, that is, aminohexanoyl-aspartic acid[dicarboxymethyl-L-Lys(aminohexyl-lactose)$_3$]$_2$, referred to as HexaLac for short.

Example 2. Conjugation of HexaLac to diBoc-NOTA

Figure 2:
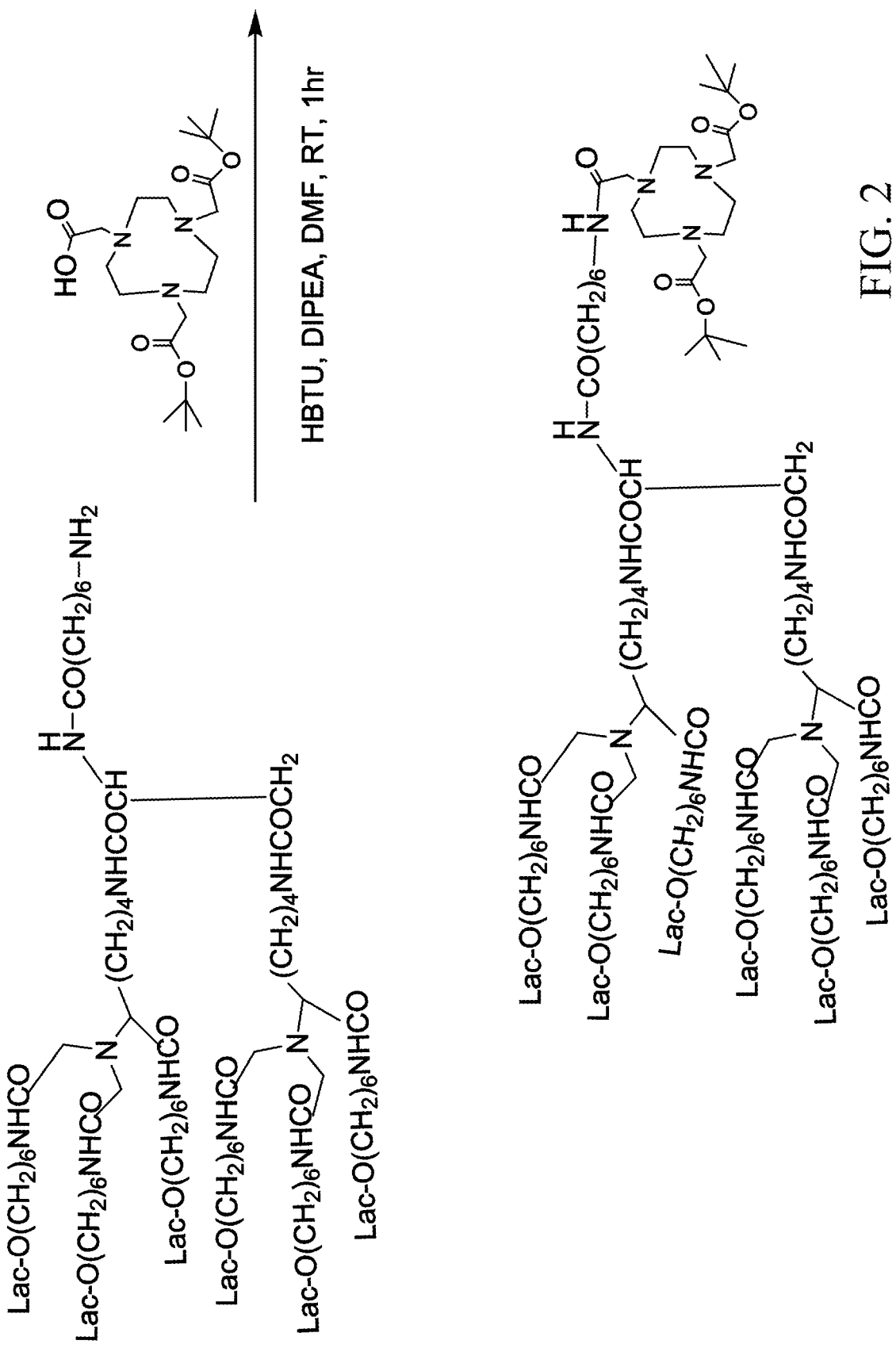
FIG. 2 shows a method for conjugating HexaLac to diBoc-NOTA.

The route for conjugating HexaLac to diBoc-NOTA is shown in FIG. 2. A two-neck flask was purged with nitrogen. HexaLac-NH$_2$ (1 eq., 10 mg, 0.003 mmol), HBTU (N,N,N,N'-Tetramethyl-O-(1H-benzotriazol-1-yl)uronium hexafluorophosphate, 2.0 eq., 2 mg, 0.006 mmol), diBoc-NOTA (di-tert-butyloxycarbonyl protected NOTA, 2 eq, 2.5 mg, 0.006 mmol), and dimethyl formamide (DMF, 0.2 mL) were added to the flask. Then, DIEA (diethylamine, 4.0 eq, 1 μL, 0.012 mmol) was added to the reaction flask and stirred for 1 hr. After the reaction was completed, ethyl acetate (EA) was added to precipitate the product. Next, the reaction system was centrifuged and the supernatant was removed. Then, EA was added again for washing, followed by centrifugation, and removal of the supernatant. The above procedure was repeated 3 times. Finally, the residue was purified by medium pressure liquid chromatography (MPLC) on a RP-18 column (MeOH/H$_2$O=40%/60%→MeOH/H$_2$O=100%/0%). The obtained product was HexaLac-diBocNOTA (10 mg in total, yield: 89%).

Figure 3:
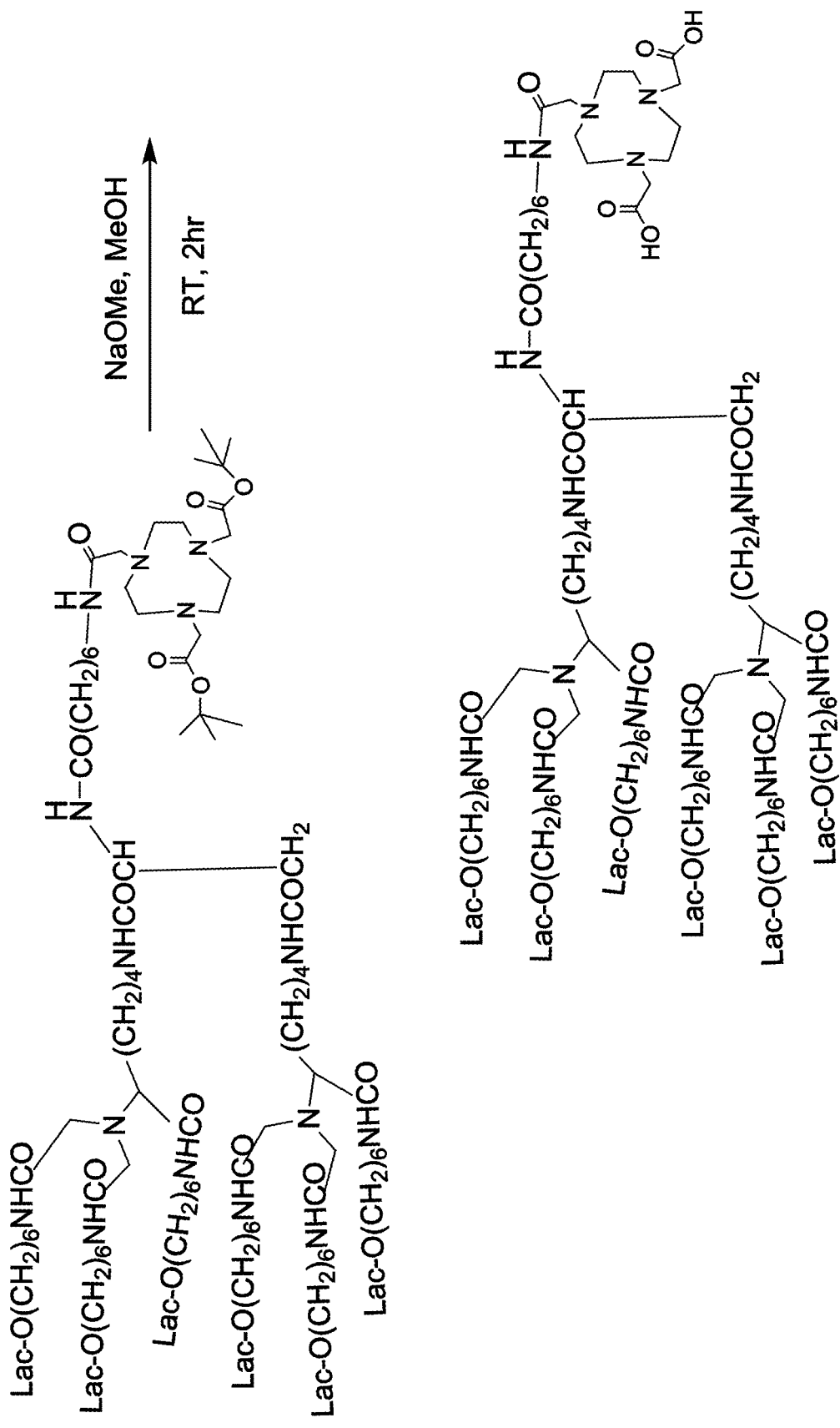
FIG. 3 shows a method for removing the protecting group Boc from HexaLac-diBocNOTA.

Next, the Boc protecting group was removed. The route for removing the Boc protecting group from HexaLac-diBocNOTA was shown in FIG. 3. First, HexaLac-diBoc-NOTA (1.0 eq, 10 mg, 0.003 mmol), and methanol (0.5 mL) was added to a reaction flask. Next, sodium methoxide (20.0 eq, 3.2 mg, 12.5 mmol) was added to the reaction flask and stirred for 2 hrs. A white solid was precipitated out. The reaction system was centrifuged and the supernatant was removed. A small amount of methanol (0.5 mL) was added again for washing and the supernatant was removed. The above procedure was repeated 3 times. The residue was purified and separated by HPLC (acetonitrile/1% TFA=5%/95%→acetonitrile/1% TFA=70%/30%). The obtained product was HexaLac-NOTA (2 mg in total, yield: 25%). However, in the method for synthesizing HexaLac-diBocNOTA with diBocNOTA, in the step of removing the protecting group, a basic or acidic reaction condition is needed, which has an impact on the HexaLac, so the stability is less good and the product cannot be obtained successfully due to the susceptibility to decomposition. Therefore, in other embodiments, no NOTA derivative protected with tert-butyl is used.

Example 3: Conjugation of HexaLac to NHS-NOTA

Figure 4:
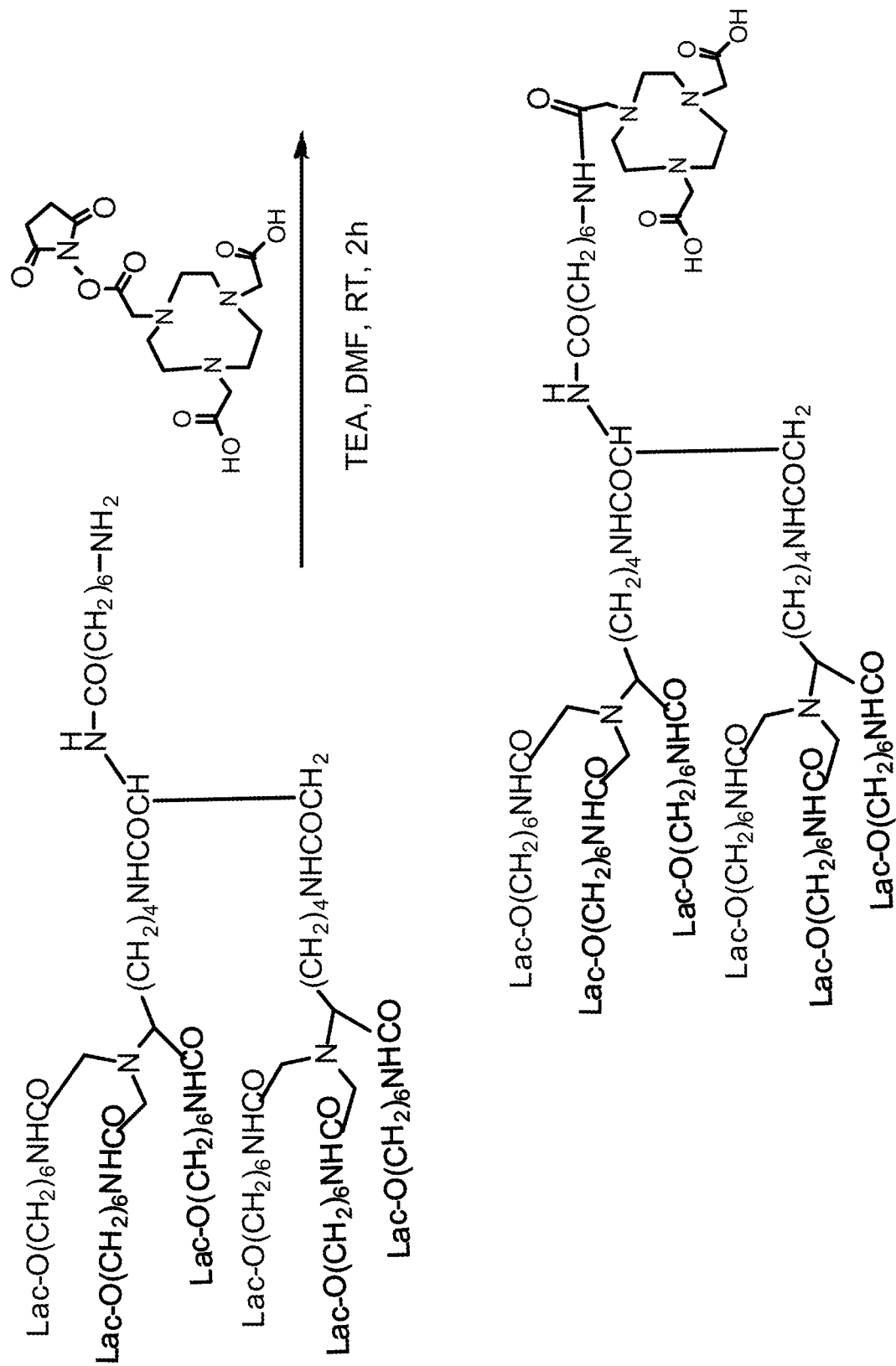
FIG. 4 shows a method for conjugating HexaLac to NHS-NOTA.

In order to avoid the failed reaction caused by a too strong reaction condition in the deprotection reaction, NHS-NOTA is used as a reactant. In particular, the HexaLac is linked in one step through reaction with the activated NHS end, so no additional deprotection reaction is needed. The route for conjugating HexaLac to NHS-NOTA is shown in FIG. 4. First, HexaLac-NH$_2$ (1 eq, 10 mg, 0.003 mmol) was fed to a reaction flask and dissolved in dimethylformamide (1 mL) and triethylamine (0.002 mL). Next, N-hydroxysucciniimide triazanonane (i.e. NHS-NOTA) (2 eq., 0.004 mg, 0.006 mmol) was added. After stirring for 2 hrs, diethyl ether was added to precipitate the product. Next, the reaction system was centrifuged and the supernatant was removed. Diethyl ether was added again for washing, followed by centrifugation, and removal of the supernatant. The above procedure was repeated 3 times. Finally, the residue was purified by MPLC on a RP-18 column (MeOH/H$_2$O=10%/90%→MeOH/H$_2$O=100%/0%). The obtained product was HexaLac-NOTA (4 mg in total, yield: 30%). However, in this example, the synthesized HexaLac-NOTA is less stable under the labeling conditions in subsequent isotope labeling procedure.

The isotope labeling experiment was further explained below. The method for radiolabeling HexaLac-NOTA with Ga-68 was as described by Yu (2015) (Yu H M, Chen J H, Lin K L, Lin W J. Synthesis of (68)Ga-labeled NOTA-RGD-GE11 heterodimeric peptide for dual integrin and epidermal growth factor receptor-targeted tumor imaging. J Labelled Comp Radiopharm 2015; 58(7): 299-303). 0.5 mL of Ga-68 (about 185 MBq) was added to 10 μL of 0.1 M HEPES buffer (pH7-7.6). Then the solution was adjusted to pH 4.0-4.5 with 0.1 M HCl. Next, 50 μg of NOTA-HexaLac was added, and ultrasonicated for 30 minutes (or heated at 90° C. for 30 min in other embodiments). The labeling efficiency in this embodiment is difficult to reach 90% or higher, and heating is needed. If the labeling is facilitated by microwave heating, although the labeling efficiency can be increased to 99% or higher, the labeled product is not stable and is prone to decomposition. In the mass spectrum, many peaks corresponding to the broken compounds are observed, suggesting that the labeled product is extremely unstable. In other words, the hexa-lactoside complex is not stable. However, if the labeling is performed at room temperature, labeling efficiency is very low because the chelating agent NOTA is in close proximity with the hexa-lactoside molecules.

Example 4: Conjugation of HexaLac to p-NCS-benzyl-NODA GA

Figure 5:
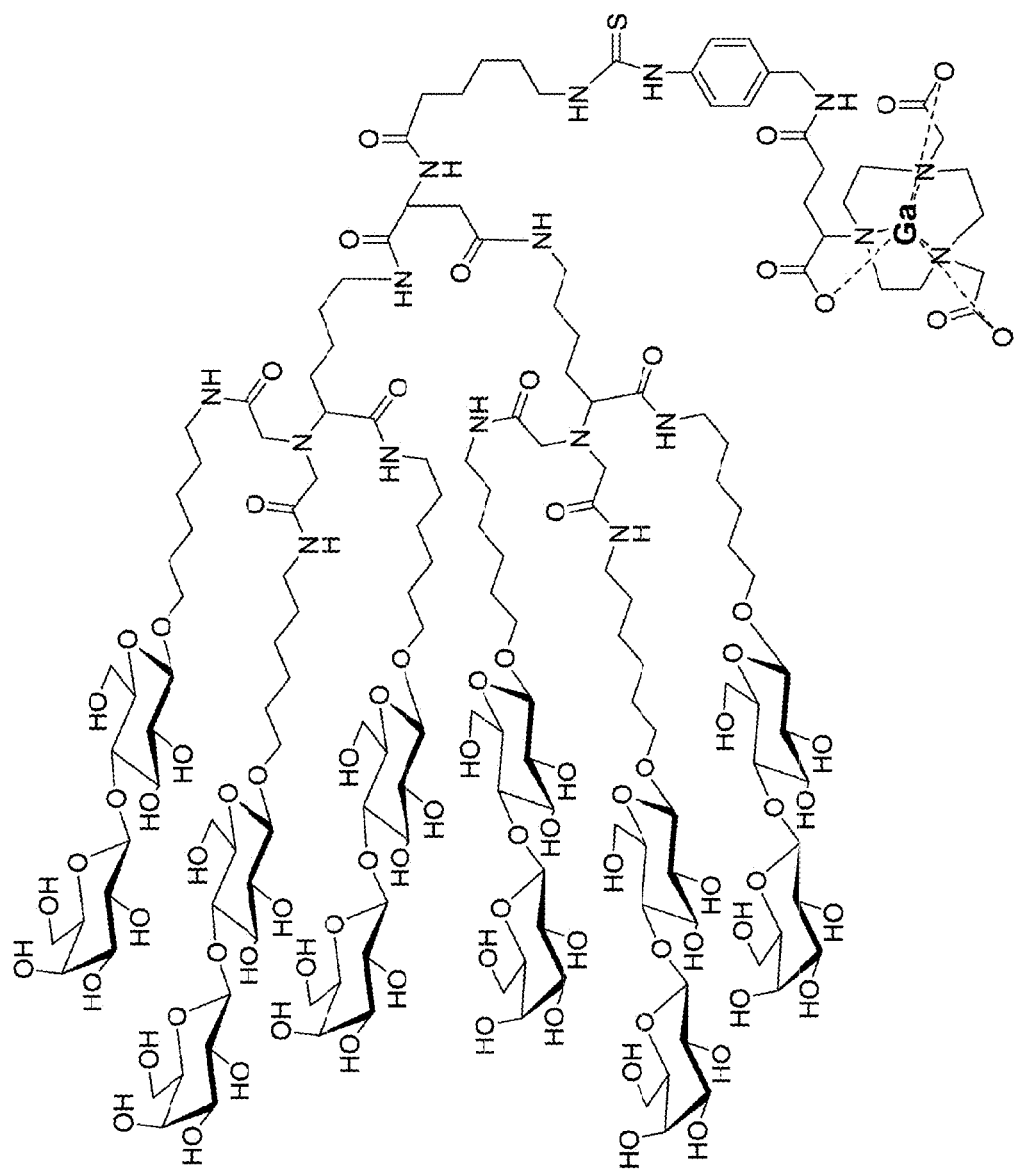
FIG. 5 shows coordination bonding of Ga-68 to HexaLac-NCS-Bn-NODA-GA.

In order to overcome the problem of the isotope labeling experiment as described above, p-NCS-NODA-GA is used as a chelating agent in the following example. On one hand, the distance between NOTA and hexa-lactoside is relatively long, which can reduce the steric hindrance caused by hexa-lactoside when a metal is chelated. On the other hand, the amino groups of hexa-lactoside is bonded to and forms a thiourea linkage with the isothiocyanate of p-NCS-NODA-GA, which is click chemistry in one pot. The steps are simplified and no any deprotection step is involved. Furthermore, six-coordination binding can stabilize the chelation of NODA-GA with Ga-68 (FIG. 5 shows the coordination bonding of Ga-68 and HexaLac-NCS-Bn-NODA-GA).

Figure 6:
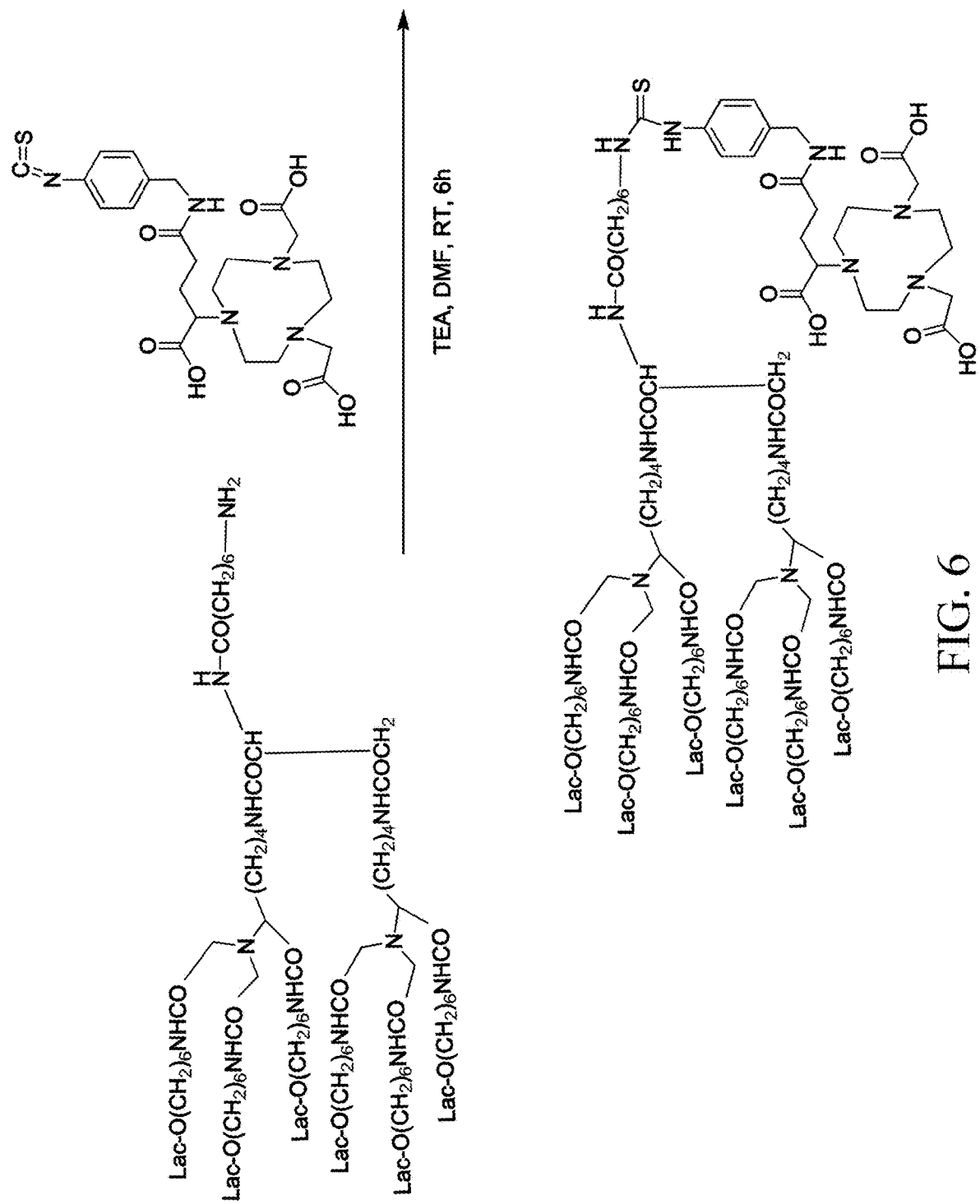
FIG. 6 shows a method for conjugating HexaLac to p-NCS-Bn-NODAGA.

The route for conjugating HexaLac to p-NCS-Bn-NODA-GA is shown in FIG. 6. First, HexaLac-NH$_2$ (39.7 mg, 12 μmol) was dissolved in triethyl amine/dimethyl formamide (0.3 mL/3 mL). Next, p-thiocyanate-benzyl-triazanonane diacetic acid-glutamic acid (p-NCS-benzyl-NODA GA, 12.6 mg, 24 μmol, Chematech, France. FW=521.59) was added, and reacted for 6 hrs with stirring. Then, diethyl ether (30 mL) was added to precipitate a solid. Next, the reaction system was centrifuged and the supernatant was removed. Diethyl ether (30 mL) was then added again, and ultrasonicated for 5 min, followed by centrifugation, and removal of the supernatant. A crude solid product was obtained. The obtained crude product was purified by MPLC, and then concentrated under reduced pressure and freeze dried to obtain HexaLac-NCS-benzyl-NODA GA (38.0 mg, 10 μmol). In this embodiment, the yield was 82%. 20 μg of Hexa-lactoside-NOTA was dissolved in 0.1% TFA/ddH$_2$O (0.5 mL), and then analyzed by LC-MS (ABI 4000Q Trap LC/MS/MS). The peak signal determined is at 1266.6[M+3H]$^{3+}$, the molecular weight is 3797.

A mass spectrum of HexaLac-NCS-Bn-NODA-GA was showed as following: $^1$H NMR (400 MHz, D$_2$O, 6): 7.34-7.32 (d, J=8.0, 2H, Ar$\underline{H}$), 7.23-7.21 (d, J=7.6, 2H, Ar$\underline{H}$), 4.41 (d, J=8.0, 6H, H$_{Lac}$-1), 4.40 (d, J=7.6, 6H, H$_{Lac}$-1), 2.81-3.94 (m, 137H), 1.22-2.54 (m, 72H). $^{13}$C NMR (400 MHz, D$_2$O, 6): 178.45 (CO), 176.42 (CO), 175.60 (CO), 174.65 (CO), 174.24 (CO), 173.23 (CO), 172.20 (CO), 171.36 (CO), 128.71 (CH, aromatic), 125.93 (CH, aromatic), 103.05 (CH, C$_{Lac}$-1), 102.18 (CH, C$_{Lac}$-1), 78.64 (CH), 75.44 (CH), 74.85 (CH), 74.59 (CH), 72.97 (CH), 72.67 (CH), 71.06 (CH), 70.58 (CH$_2$, C$_{Ah}$-1), 68.66 (CH), 66.95 (CH), 66.39 (CH), 61.09 (CH$_2$), 60.29 (CH$_2$), 57.83 (CH$_2$), 56.03 (CH$_2$), 51.48 (CH$_2$), 51.01 (CH), 49.45 (CH$_2$), 46.80 (CH$_2$), 42.70 (CH$_2$), 39.28 (CH$_2$), 39.15 (CH$_2$), 37.76 (CH$_2$), 35.50 (CH$_2$), 32.81 (CH$_2$), 28.83 (CH$_2$), 28.43 (CH$_2$), 26.00 (CH$_2$), 25.65 (CH$_2$), 25.56 (CH$_2$), 25.04 (CH$_2$), 24.87 (CH$_2$), 23.24 (CH$_2$), 23.09 (CH$_2$). HSQC: Correlation 128.71 (CH, aromatic) to 7.33 (d, J=8.0, 2H, Ar$\underline{H}$), 125.93 (CH, aromatic) to 7.22 (d, J=7.6, 2H, Ar$\underline{H}$), 103.05 (CH, C$_{Lac}$-1) to 4.41 (d, J=8.0, 6H, H$_{Lac}$-1), 102.18 (CH, C$_{Lac}$-1) to 4.40 (d, J=7.6, 6H, H$_{Lac}$-1).

Figure 7A:
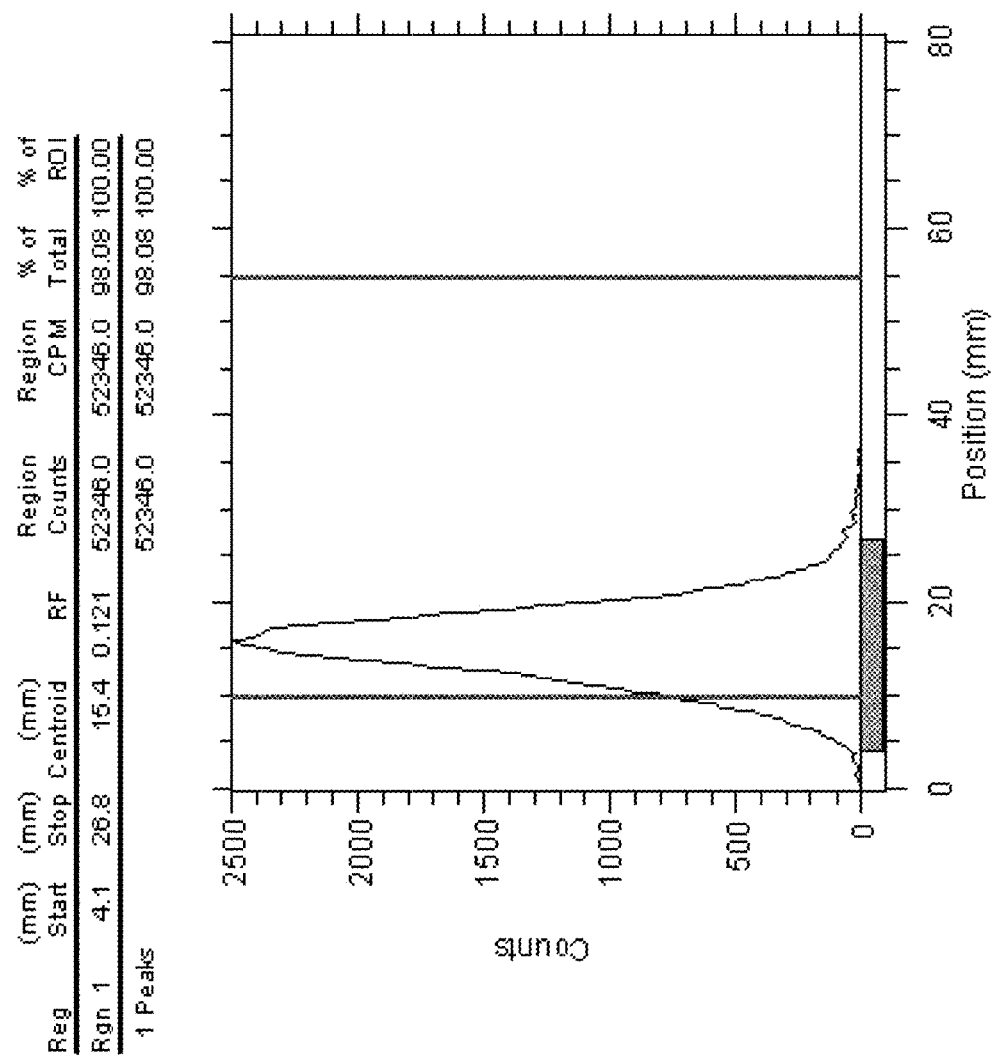
FIG. 7A shows radiochemical purity analysis of Ga-68-HexaLac-NC S-Bn-NODA-GA.
Figure 7B:
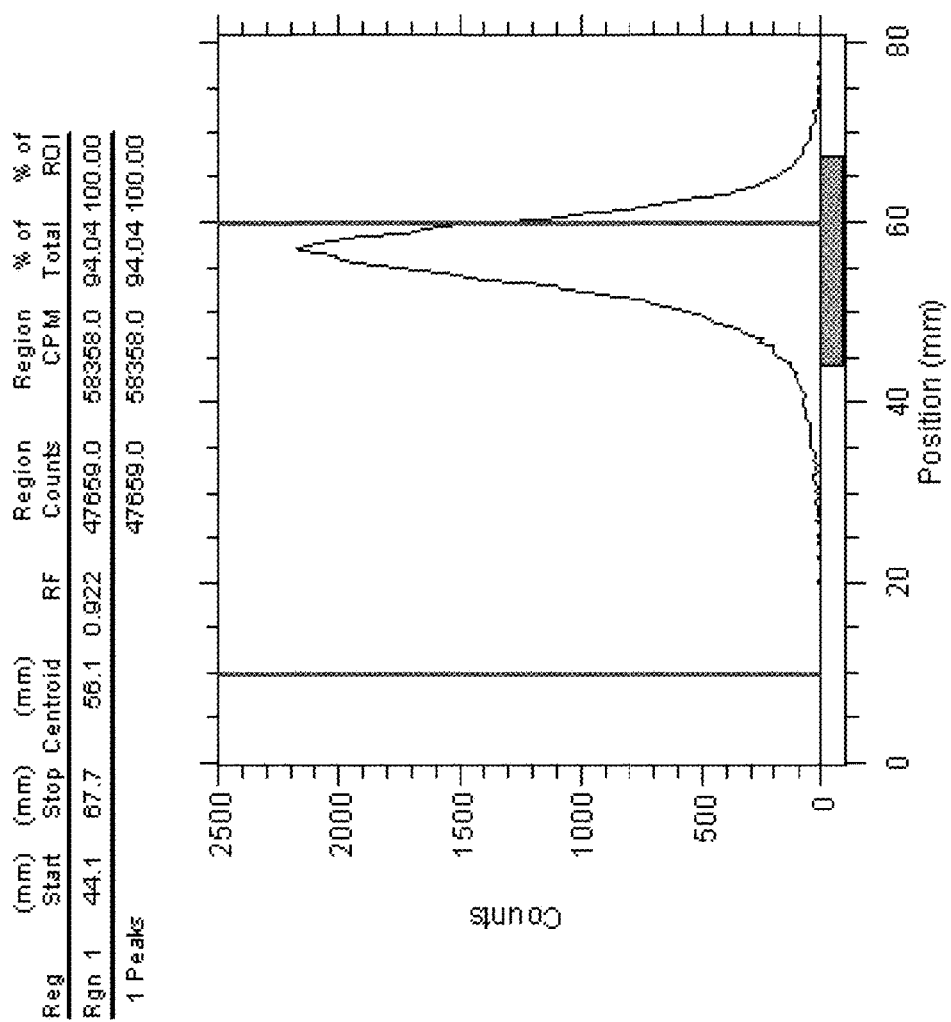
FIG. 7B shows radiochemical purity analysis of free Ga-68.
Figure 8:
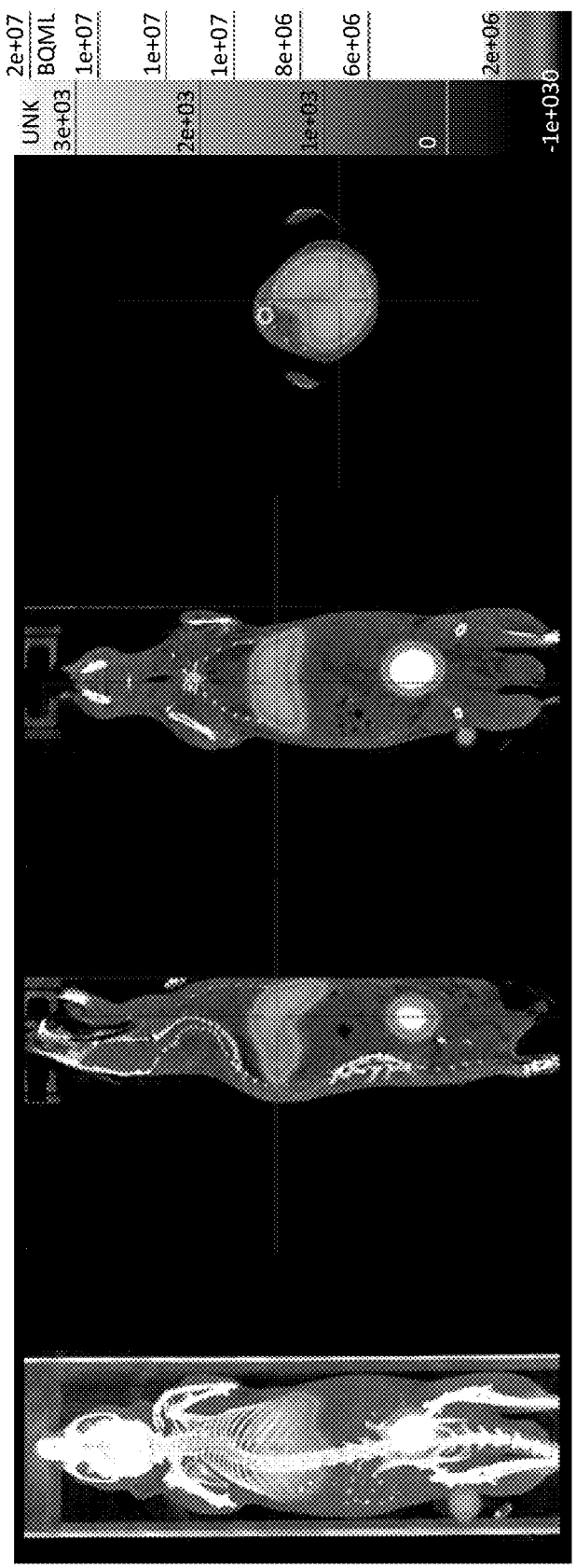
FIG. 8 shows PET/CT imaging with Ga-68-HexaLac-NCS-Bn-NODA-GA.
Figure 9:
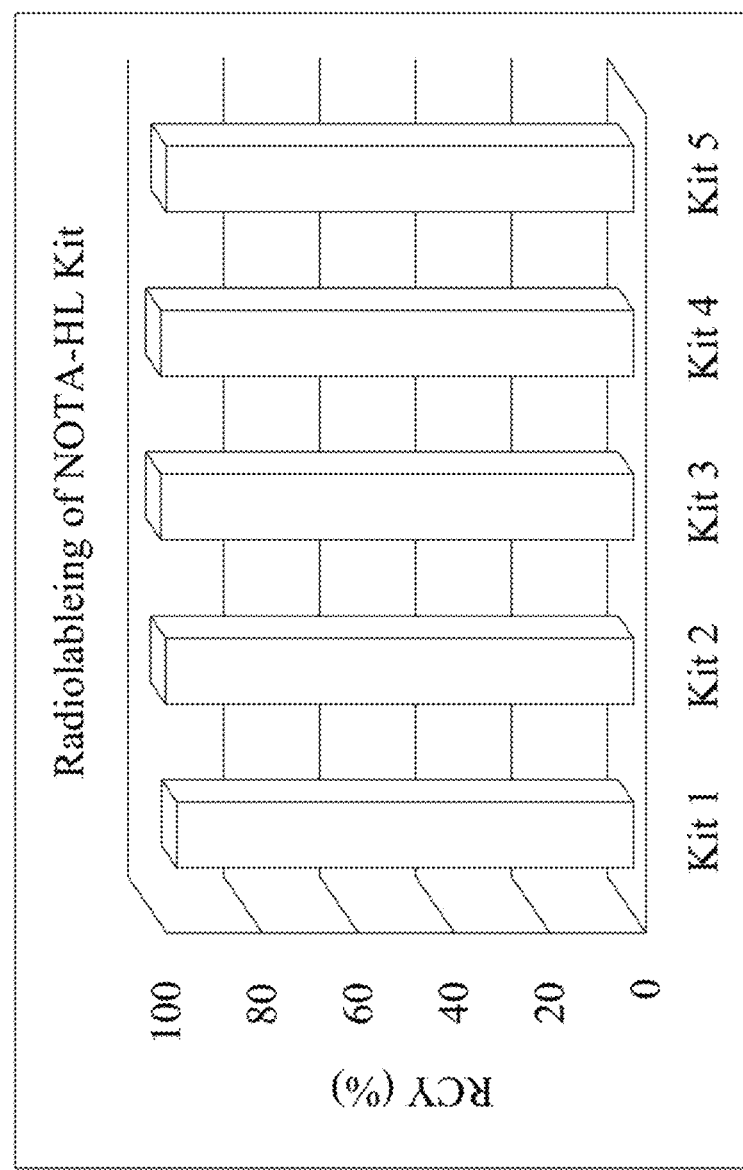
FIG. 9 shows the reproducibility of the labeling efficiency of HexaLac-NCS-Bn-NODA-GA with Ga-68.
Figure 10:
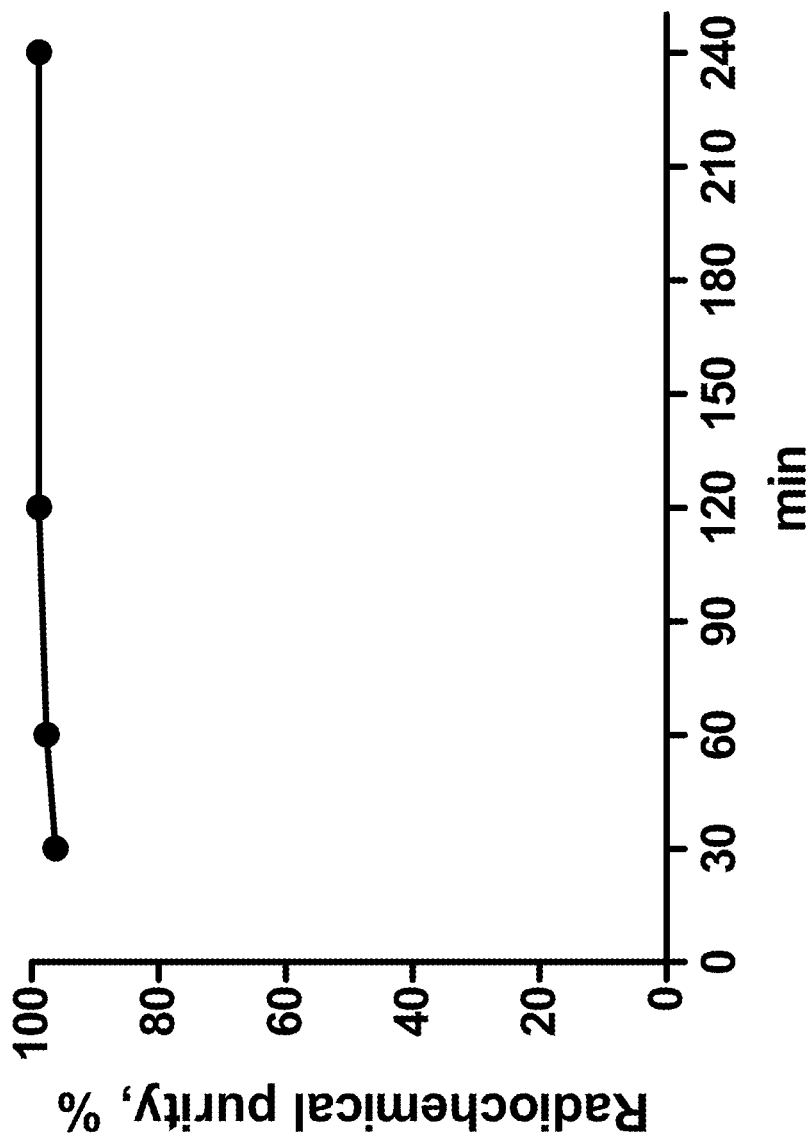
FIG. 10 shows the stability of HexaLac-NCS-Bn-NODA-GA labeled with Ga-68 over times.

HexaLac-NCS-benzyl-NODA-GA was labeled with Ga-68. The labeling process was as described in Knetsch (2011) (Knetsch P A, Petrik M, Griessinger C M, Rangger C, Fani M, Kesenheimer C, et al. [$^{68}$Ga]NODAGA-RGD for imaging alphavbeta3 integrin expression. Eur J Nucl Med Mol Imaging 2011; 38(7):1303-12). A gallium (Ga-68) chloride solution (0.5 mL, 10±1 mCi/mL) (NODAGA-RGD for imaging alphavbeta3 integrin expression. Eur J Nucl Med Mol Imaging 2011; 38(7):1303-12) was drawn by a syringe, added to and completely dissolved in HexaLac-NCS-benzyl-NODA-GA (40 μg) and sodium acetate (13.61 mg) in a freeze drying ampoule in 1-2 minutes, and stood for 15 min. Then, 1.5 mL of normal saline was added and mixed uniformly, and then sampled for analysis and imaging. The radiochemical purity analysis of the labeled product is shown in FIGS. 7A and 7B. The imaging results are shown in FIG. 8. The labeling was performed five times consecutively, using 40 μgNOTA-HL and Ga-68 with an activity of 5±0.5 mCi. The labeling effect was stable, and the radiochemical purity of the product was >95%. The reproducibility of the labeling efficiency is shown in FIG. 9. The stability over time is shown in FIG. 10. As shown, the labeled product has good stability. Regardless of the addition of stabilizers, the labeled product still has a radiochemical purity of 90% or greater after 4 hrs.

Example 5: Radiochemical Purity Test of Ga-68-HexaLac-NC S-benzyl-NODA-GA 10 mL of 0.1M EDTA was added to a developing tank, and an origin and a solvent front were marked at 1 cm and 5 cm of the RP-TLC plate. Then, a small amount of sample (1-2 μL) was dotted on the origin of the RP-TLC plate, and then the plate was placed in the developing tank by using forceps. When the developing solution reached the solvent front, the plate was removed by using forceps and dried in an oven. The ITLC-SG plate was scanned by using a radio-TLC imaging scanner, and the spectrum was collected over 1 min. The result was calculated through a formula below:

$$\text{Radiochemical purity}(\%) = \frac{A}{B} \times 100\%$$

A: The count area of the $^{68}$Ga-hexa-lactoside peak (Rf=0.0-0.2)

B: The count area of all peaks

Example 6: PET Imaging with Ga-68-HexaLac-NCS-benzyl-NODA-GA

The Ga-68-HexaLac-NCS-benzyl-NODA GA (15 μCi/g) was injected into mice through the tail vein. After injection, PET/CT imaging was performed immediately for 15 min. During the imaging process, the test animals were anesthetized with isoflurane. After imaging, the PET/CT images were fused. The imaging results are shown in FIG. 8.

Although embodiments of the present invention have been illustrated and described, various modifications and improvements will occur to those skilled in the art. The present invention is not intended to be limited to the particular forms illustrated, and the modifications made without departing from the spirit and scope of the present invention all fall within the scope as defined by the appended claims In view of the above, the present invention has not been found in similar products in terms of the characteristics and combination as a whole, and has not been disclosed before the application. Since the present invention meets the statutory requirements of the Patent Law, an application for invention patent is filed according to the Patent Law.

Although the embodiments of the present invention have been disclosed above, they are not intended to limit the present invention. Any modifications made by persons skilled in the art to the shapes, structures, and features without departing from the spirit and scope of the present invention fall within the scope of the present invention as defined in appended claims.

What is claimed is:

1. A hexa-lactoside-triazanonane triacetic acid (NOTA) derivative, having a structure of:

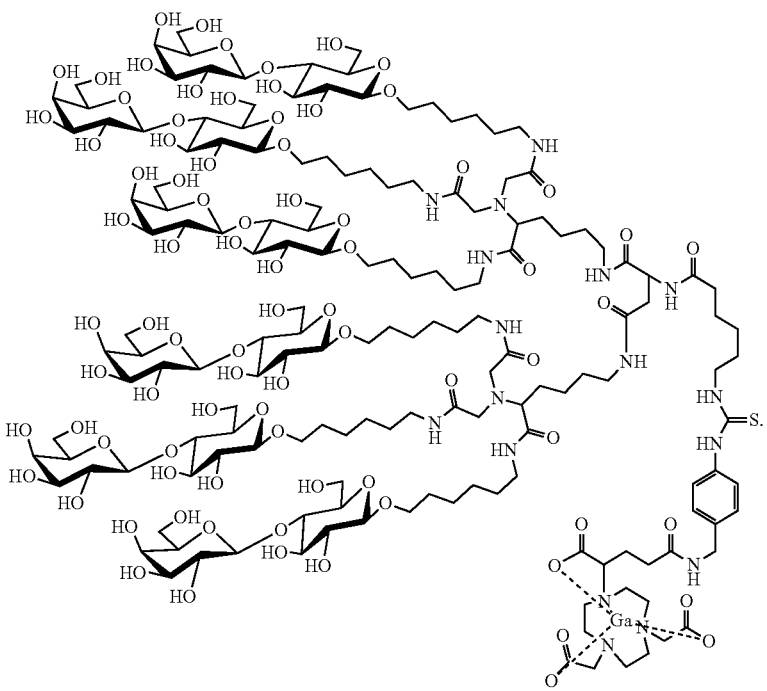

2. A hexa-lactoside positron emission tomography (PET) imaging agent for a liver receptor, having a structure of:
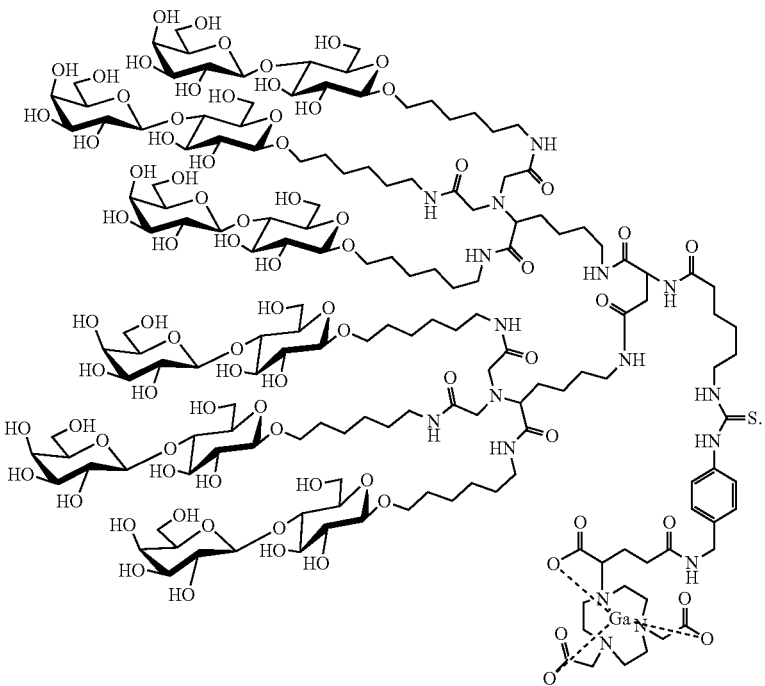
3. The imaging agent according to claim 2, which is prepared by the steps of:
reacting 3-valent Ga-68 and a triazanonane triacetic acid (NOTA) conjugate of six chains of lactose with sodium acetate buffer in a freeze drying ampoule at room temperature.
* * * * *